United States Patent

Dolazza et al.

[19]

[11] Patent Number: 5,991,358
[45] Date of Patent: Nov. 23, 1999

[54] DATA ACQUISITION SYSTEM FOR GENERATING ACCURATE PROJECTION DATA IN A CT SCANNER

[75] Inventors: Enrico Dolazza, Boston; Hans J. Weedon, Salem; Douglas Q. Abraham, Topsfield, all of Mass.

[73] Assignee: Analogic Corporation, Peabody, Mass.

[21] Appl. No.: 09/001,863

[22] Filed: Dec. 31, 1997

[51] Int. Cl.[6] .................................................. A61B 6/03
[52] U.S. Cl. ............................ 378/19; 378/19; 378/901
[58] Field of Search .............................. 378/4, 15, 19, 378/901

[56] References Cited

U.S. PATENT DOCUMENTS

| 4,532,644 | 7/1985 | Yamaguchi et al. | 378/16 |
|---|---|---|---|
| 4,547,893 | 10/1985 | Gordon | 378/19 |
| 5,053,770 | 10/1991 | Mayer et al. | 341/118 |
| 5,099,505 | 3/1992 | Seppi et al. | 378/65 |
| 5,142,286 | 8/1992 | Ribner et al. | 341/143 |
| 5,187,482 | 2/1993 | Tiemann et al. | 341/143 |
| 5,257,026 | 10/1993 | Thompson et al. | 341/118 |
| 5,274,375 | 12/1993 | Thompson | 341/143 |
| 5,432,339 | 7/1995 | Gordon et al. | 250/231.13 |

*Primary Examiner*—David Vernon Bruce
*Attorney, Agent, or Firm*—Lappin & Kusmer LLP

[57] ABSTRACT

A data acquisition system for use in a CT scanner comprises an analog-to-digital converter for generating digital signals in response to analog signals representative of projection data taken at a relatively constant sampling rate; and an interpolation filter for generating projection data for a plurality of predetermined projection angles as a function of the digital signals irrespective of the sampling rate.

20 Claims, 8 Drawing Sheets

DATA ACQUISITION SYSTEM FOR GENERATING ACCURATE PROJECTION DATA IN A CT SCANNER

FIELD OF THE INVENTION

The present invention relates generally to a data acquisition system (DAS) for use with a computed tomography (CT) scanner. More particularly, the invention relates to an improved DAS that includes an analog-to-digital converter for sampling the analog detector output signals at a constant frequency or rate, and an interpolation filter for interpolating the samples irrespective of the sampling rate so as to generate projection data corresponding to desired projection angles.

BACKGROUND OF THE INVENTION

Figure 1:
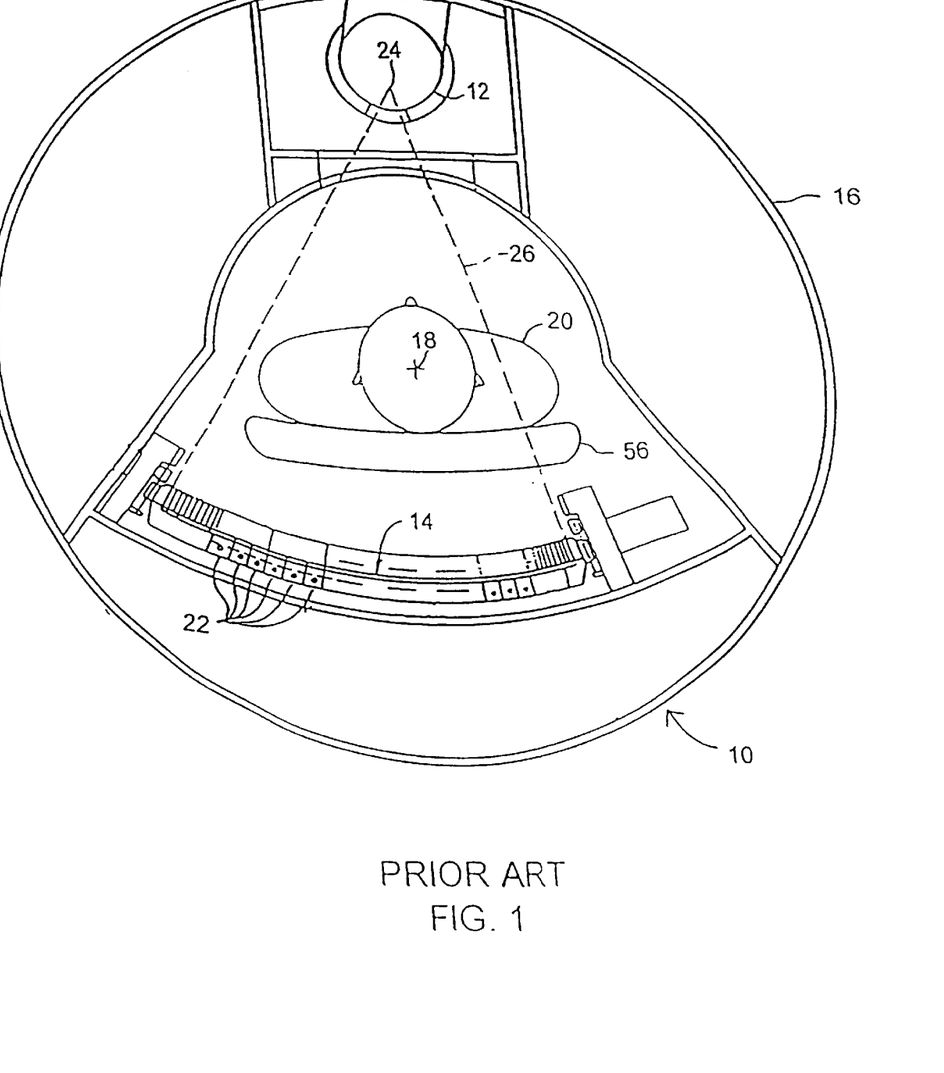
FIG. 1 shows an axial view of a prior art CT scanner.

FIG. 1 shows an axial view of a typical prior art third generation CT scanner 10 that includes an X-ray source 12 and an X-ray detector system 14 secured respectively to diametrically opposite sides of an annular-shaped disk 16. The disk is rotatably mounted within a gantry support (not shown) so that during a tomographic scan, the disk continuously rotates about a rotation axis 18 (which is normal to the plane of the page in FIG. 1) while X-rays pass from the source 12 through an object, such as a human patient 20 positioned within the opening of the disk, to the detector system 14.

The detector system 14 typically includes an array of individual detectors 22 disposed, for example, as a single row in the shape of an arc of a circle having a center of curvature at the point 24, referred to as the "focal spot", where the radiation emanates from the X-ray source 12. Other detector systems are known. The X-ray source and the array of detectors are positioned so that the X-ray paths between the source and each of the detectors all lie in the same plane (hereinafter the "rotation plane" or "scanning plane") which is normal to the rotation axis 18 of the disk. Since the X-ray paths originate from what is substantially a point source and extend at different angles to the detectors, the X-ray paths form a "fan beam" 26 that is incident on the detector system 14. The X-rays incident on a single detector at a measuring interval during a scan are commonly referred to as a "ray", and each detector generates an analog output signal indicative of the intensity of its corresponding ray. Since each ray is partially attenuated by all the mass in its path, the analog output signal generated by each detector is representative of an integral of the density of all the mass disposed between that detector and the X-ray source (i.e., the density of the mass lying in the detector's corresponding ray path) for that measuring interval.

The analog output signals generated by the X-ray detectors are normally processed by a signal processing portion (not shown in FIG. 1) of the CT system. The signal processing portion usually includes an analog low pass filter and a DAS. The low pass filter removes high frequency components from the analog output signals generated by the X-ray detectors, and the DAS filters the analog output signals generated by the low pass filter to improve their signal-to-noise ratio. One such DAS is described in U.S. Pat. No. 4,547,893, which is assigned to the assignee of the present invention. Other types of DASs are well known. The DAS also normally samples the filtered signals to generate digital output signals representative of the acquired projection data during each projection. The digital output signals generated by the DAS are referred to herein as "projection data signals". The collection of all the projection data signals at a measuring interval is commonly referred to as a "projection" or a "view", and the angular orientation of the X-ray source 12 and detector system 14 on the disk 16 corresponding to a particular projection or view is referred to as the "projection angle".

During a single tomographic scan, ideally the disk 16 rotates smoothly and continuously around the object being scanned allowing the scanner 10 to generate a plurality of projections precisely at a corresponding plurality of projection angles. In a typical tomographic scan, the disk rotates at least 360° around the object being scanned, and the scanner ideally generates a new projection every time the disk rotates an equal incremental amount referred to as Δθ. For example, where Δθ is 0.125 degrees for a 360° scan, the scanner generates 2,880 (i.e., eight times 360) projections. The sampling interval between measuring adjacent projections (i.e., the time required for the disk to rotate through an angle of Δθ) is typically on the order of a millisecond.

Using well known algorithms, such as the inverse Radon transform, a tomogram may be generated from the data acquired at all the projections measured at the corresponding projection angles. A tomogram is representative of the density of a two dimensional "slice" of the object being scanned. The process of generating a tomogram from the projections is commonly referred to as "filtered back projection" or "reconstruction", since the tomogram may be thought of as being reconstructed from the projection data. The signal processing portion normally includes a back projector for generating the tomograms from the projections.

It is generally assumed that there are at least two requirements for acquiring data during a scan. First, the data must be acquired with the best possible dynamic range and the best possible signal-to-noise ratio. Secondly, the data must be taken at precise and known angles of rotation so that a simpler and faster reconstruction algorithm can be used. These reconstruction algorithms generally assume that the projection data used to reconstruct a single tomogram are generated at equally spaced projection angles (i.e., that the disk 16 rotates by exactly, no more and no less than, Δθ between the generation of data for each successive projection). If the projections used to reconstruct a tomogram are not generated at equally spaced projection angles, the resulting tomogram will normally include unwanted artifacts. However, prior art CT scanners have had difficulty in generating projections precisely at equally spaced projection angles.

There are at least three sources of possible errors relating to the acquisition of data at precise and known angles of rotation. First, the rotational speed of the disk, may not be constant, and therefore making projection measurements at equal time intervals, will not necessarily result in projection data at precisely equal angular position intervals of Δθ. Second, the measurement of the angles may be inaccurate. Third, the angle markers and position measurements may not be precise enough.

Figure 2:
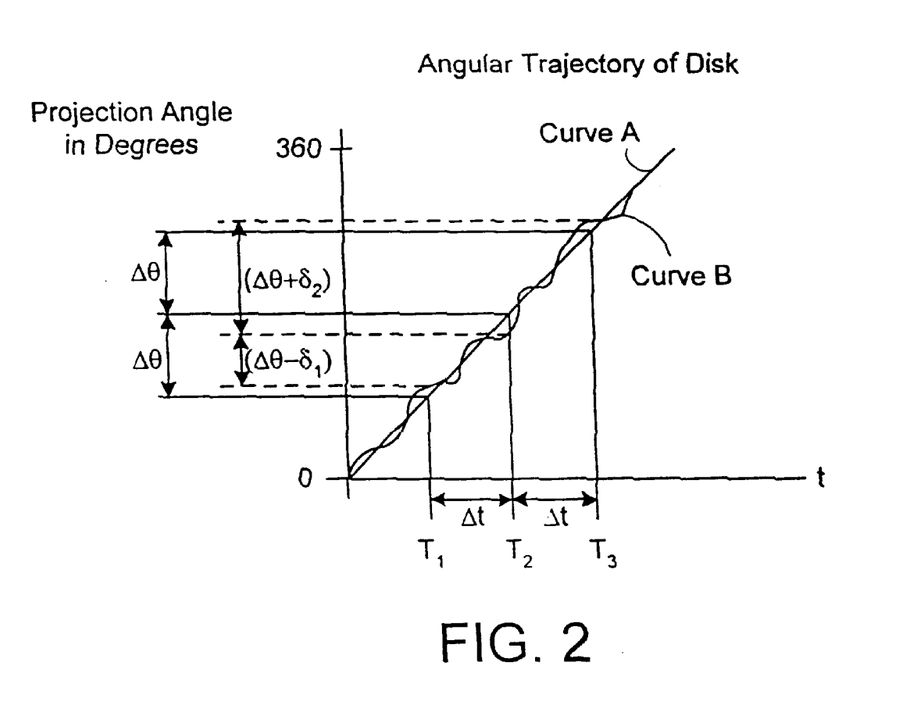
FIG. 2 shows a graph that illustrates the rotational irregularities of the disk normally associated with CT scanners.

With regard to the first source of error, as stated above, during a typical tomographic scan, the disk 16 rotates at least 360°, and this rotation is normally accomplished in a time period on the order of two seconds. In practice it is extremely difficult to control the rotation of disk 16 so that the disk rotates with precise constant angular velocity. Rather, the rotational speed of disk 16 is typically characterized by some irregularity, or phase noise, sometimes referred to as jitter. FIG. 2 shows a graph that illustrates the effects of this rotational irregularity. The Y-axis of FIG. 2 represents the angular orientation of the disk 16 and the X-axis represents time during a tomographic scan. An ideal, linear, constant angular velocity trajectory for disk 16 is shown in FIG. 2 by Curve A, i.e., a straight line. Curve B in FIG. 2 illustrates an angular trajectory for disk 16 that is characterized by rotational irregularity. If disk 16 follows the ideal trajectory of Curve A, projections generated at constant rate or frequency (or at sampling times that are equally spaced apart in time) will be generated at equally spaced projection angles. As shown in FIG. 2, if three projections are generated at sampling times $T_1$, $T_2$, and $T_3$, where these sampling times are separated by intervals of equal length $\Delta t$, the three projections will be equally separated in terms of their associated projection angles by equal angular intervals, each of $\Delta \theta$. However, projections generated at these sampling times when the disk follows the non-ideal trajectory of Curve B will not be equally separated in terms of their projection angle. As shown by the example shown in FIG. 2, projections generated at times $T_1$ and $T_2$ will have associated projection angles that are separated by an angular interval of ($\Delta \theta - \delta_1$), whereas projections generated at times $T_2$ and $T_3$ will have associated projection angles separated by an angular interval of ($\Delta \theta + \delta_2$). So the rotational irregularity of disk 16 causes projections generated at a constant rate or frequency to be unequally angularly spaced apart in terms of their associated projection angles. The magnitude of the rotational irregularity present in most, if not all, prior art CT scanners is normally sufficiently large to significantly degrade the quality of tomograms produced using projections generated at a constant rate or frequency.

Figure 3:
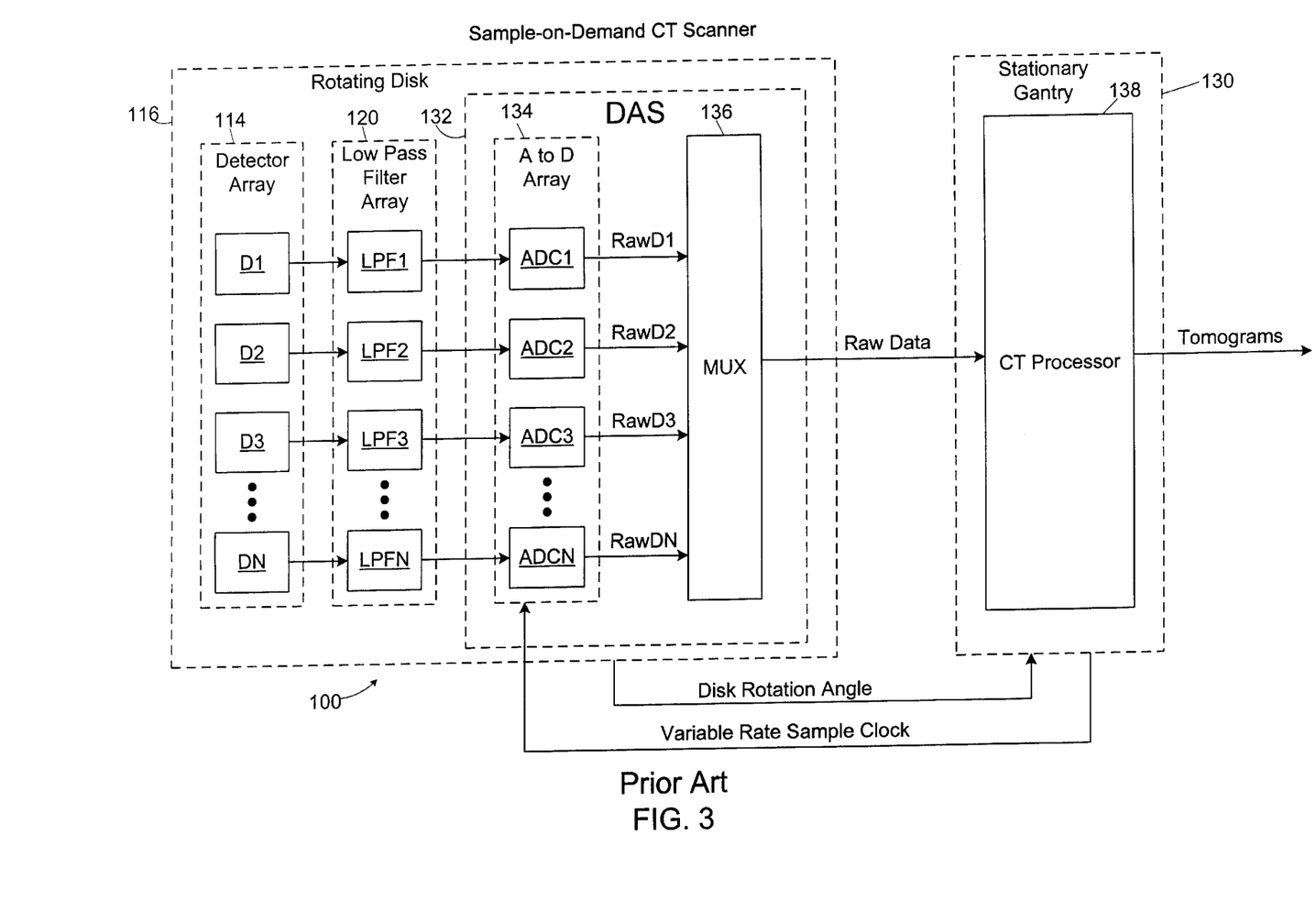
FIG. 3 shows a block diagram of a portion of a prior art sample on demand CT scanner.

FIG. 3 shows a block diagram of another prior art CT scanner 100 that provides compensation for the rotational irregularity of the disk. Scanner 100 includes a rotating disk 116 which rotates relative to a stationary gantry 130. A detector system 114, a low pass filter array 120, a DAS 132, and an X-ray source (such as source 12 which is shown in FIG. 1) are mounted on, and rotate with, disk 116. Stationary gantry 130 includes a computer or CT processor 138 for running the reconstruction algorithm with the raw data received from the disk. DAS 132 is illustrated as including a plurality or array 134 of analog-to-digital converters and a multiplexer 136. As is well known, the DAS may also include additional components such as the filters described in the above-referenced U.S. Pat. No. 4,547,893. Detector system 114 is an N-channel linear array including N individual detectors Di, for all i from one to N. Similarly, low pass filter array 120 and converter array 134 are N-channel arrays including N individual filters LPFi and analog-to-digital converters ADCi, respectively, for all i from one to N.

During a tomographic scan, while the disk 116 rotates through each of a plurality of projection angles, the detector array 114 generates N analog output signals that are applied to the low pass filter array 120. Specifically, the analog signal in the ith channel generated by the ith channel detector Di is applied to the ith channel low pass filter LPFi, for all i from one to N. The ith low pass filter LPFi receives the analog signal generated by detector Di and generates therefrom a filtered analog signal that is applied to the ith analog-to-digital converter ADCi, for all i from one to N. The ith analog-to-digital converter ADCi samples the filtered signal generated by the ith filter LPFi to generate a sampled raw data signal RawDi, for all i from one to N. The ith raw data signal RawDi includes a set of samples, or data points, RawDi(Tj) collected as sampling times Tj for all j from 1 to J, where J represents the total number of projections per scan. At any given sampling time Tj, the collection of the N data points RawDi(Tj), for all i from one to N, may be thought of as forming a single projection generated at a projection angle corresponding to the sampling time Tj. The N data points RawDi(Tj) in a projection are applied in time multiplexed fashion, via multiplexer 136, to the processor 138 on the stationary gantry 130. As is well known, multiplexer 136 is useful for reducing the number of connections between the rotating disk 116 and the stationary gantry 130. CT processor 138 generates tomograms from the projection data collected by rotating disk 116.

Also mounted in disk 116 is a system (not shown) for measuring the angular orientation of the disk in real time and for generating a Disk Rotation Angle signal that is representative of this angular orientation. Examples of prior art systems for generating the Disk Rotation Angle signal are disclosed in U.S. Pat. No. 5,432,339 issued Jul. 11, 1995 in the names of Bernie Gordon, David Winston, Paul Wagoner and Douglas Abraham and entitled Apparatus for and Method of Measuring Geometric, Positional and Kinematic Parameters of a Rotating Device; and pending U.S. patent application Ser. No. 08/948,493 filed Oct. 10, 1997 in the names of Geoffrey A. Legg, Gerard P. Riley, and Hans J. Weedon and entitled Measurement and Control System for Controlling System Functions as a Function of Rotational Parameters of a Rotating Device (Attorney's Docket No. ANA-139), both the prior patent and application being assigned to the present assignee. These systems sense markers as the disk rotates, and generate a rotation angle signal, similar to the Disk Rotation Angle signal mentioned above, when the relevant markers corresponding the projection angles are sensed. This Disk Rotation Angle signal is applied to the CT processor 138. The processor 138 monitors the orientation of disk 116 and generates a Variable Rate Sample Clock signal that is applied to and controls the operation of the analog-to-digital converter array 134. Processor 138 controls the analog-to-digital converter array 134 (via the Variable Rate Sample Clock signal) so that the converter array 134 generates projections (i.e., samples the analog filtered signals) at equally spaced projection angles. As illustrated by FIG. 2, when the disk rotation is characterized by irregularities, such equally spaced projections can not be generated by sampling at constant frequency. Rather, stationary gantry 130 continually adjusts the phase or frequency of the Variable Rate Sample Clock signal in response to detected disk rotational irregularity (as measured by the Disk Rotation Angle signal) so that the converter array 134 generates projections at the desired projection angles. Since the projections in scanner 100 are not generated at constant frequency (i.e., are not generated at equally spaced time intervals), scanner 100 is referred to as a "sample-on-demand" type scanner.

In principle, sample-on-demand scanners can provide effective compensation for disk rotational irregularities. However, there are several problems associated with sample-on-demand scanners of the type shown in FIG. 3. One problem relates to the interaction of the low pass filter array 120 and the analog-to-digital converter array 134. The low pass filters in array 120 are each characterized by a transfer function, and the analog-to-digital converters in array 134 are each characterized by another transfer function. The transfer function used to generate each raw data signal RawDi is essentially a combination of the corresponding low pass filter transfer function and analog-to-digital converter transfer function. The low pass filter transfer function is normally selected so that any signal components above a selected frequency $f_{max}$ in the detector output signals are suppressed in the filtered signals. The selected frequency $f_{max}$ is normally related to the sampling frequency used by the analog-to-digital converter array 134 to insure that high frequency components in the detector output signals are not aliased into the raw data signals.

The low pass filters in array 120 are normally implemented using analog RC (resistor-capacitor) networks, and the low pass filter transfer function of each filter is determined by the values of the components of the corresponding RC network. The analog-to-digital converter transfer function is in part a function of the phase and frequency of the Variable Rate Sample Clock signal. So, when a constant frequency, stable phase, Variable Rate Sample Clock signal is applied to analog-to-digital converter array 134, the same transfer function is used to generate every data point RawDi (Tj), for all channels i and for all sampling times j. However, adjusting the phase or frequency of the Variable Rate Sample Clock signal during a CT scan will prevent all of the data points RawDi(Tj) from being generated using the same transfer function. For example, the transfer function used to generate the data point RawD1(T5) may be different than the transfer function used to generate the later data point RawD1 (T7). Ideally, when the phase or frequency of the Variable Rate Sample Clock signal is varied (and the analog-to-digital converter transfer function is correspondingly varied) a compensatory change should be introduced into the low pass filter transfer function to insure that every data point RawDi(Tj) (and every projection) is generated using the same combined transfer function. However, since the low pass filter transfer function is determined by the particular RC network used to implement the filters, there is no simple way to introduce the desired time varying changes to the low pass filter transfer function corresponding to variations in the phase or frequency of the Variable Rate Sample Clock signal.

So, while varying the phase and frequency of the Variable Rate Sample Clock signal is desirable to insure that all projections in a scan are generated at precisely equally spaced projection angle intervals, this variance of the Variable Rate Sample Clock signal prevents all projections from being generated using the same combined transfer function. This tends to increase artifacts and reduce the signal-to-noise ratio, in the resulting tomograms.

Another problem with sample-on-demand scanner of the type shown in FIG. 3 is that the analog-to-digital converters in array 134 do not operate at a constant frequency, but instead must operate at a variable phase or frequency under control of the Variable Rate Sample Clock signal. Such converters are more expensive to construct than constant frequency analog-to-digital converters. The cost and complexity of CT scanners could be reduced if the analog-to-digital converters could operate at a constant sampling frequency. However, this has not been considered possible in prior art scanners because of the problems associated with disk rotation irregularities.

These and other problems with, and limitations of, the prior art CT scanners are overcome with the CT scanner of this invention.

OBJECTS OF THE INVENTION

It is an object of the present invention to substantially reduce or overcome the above-identified problems of the prior art.

Another object of the present invention is to provide an improved system for generating projections in CT scanners.

And another object of the present invention is to provide an improved CT scanner that decouples data acquisition from projection generation.

Yet another object of the present invention is to provide an improved CT scanner that samples the analog output signals generated in response to the X-ray detectors using a substantially constant frequency and then interpolates between these samples to generate projections at desired projection angles.

SUMMARY OF THE INVENTION

These and other objects are provided by an improved CT scanner that includes an analog-to-digital converter that samples the output signals generated in response to the X-ray detectors using a constant frequency. The scanner also includes a digital filter for interpolating between the samples generated by the analog-to-digital converters to generate projections at desired projection angles.

In accordance with another aspect of the invention an improved DAS is provided. The DAS includes a digital filter for interpolating between samples generated by analog-to-digital s provide.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE DRAWINGS

For a fuller understanding of the nature and objects of the present invention, reference should be had to the following detailed description taken in connection with the accompanying drawings in which the same reference numerals are used to indicate the same or similar parts wherein.

DETAILED DESCRIPTION OF THE DRAWINGS

Figure 4:
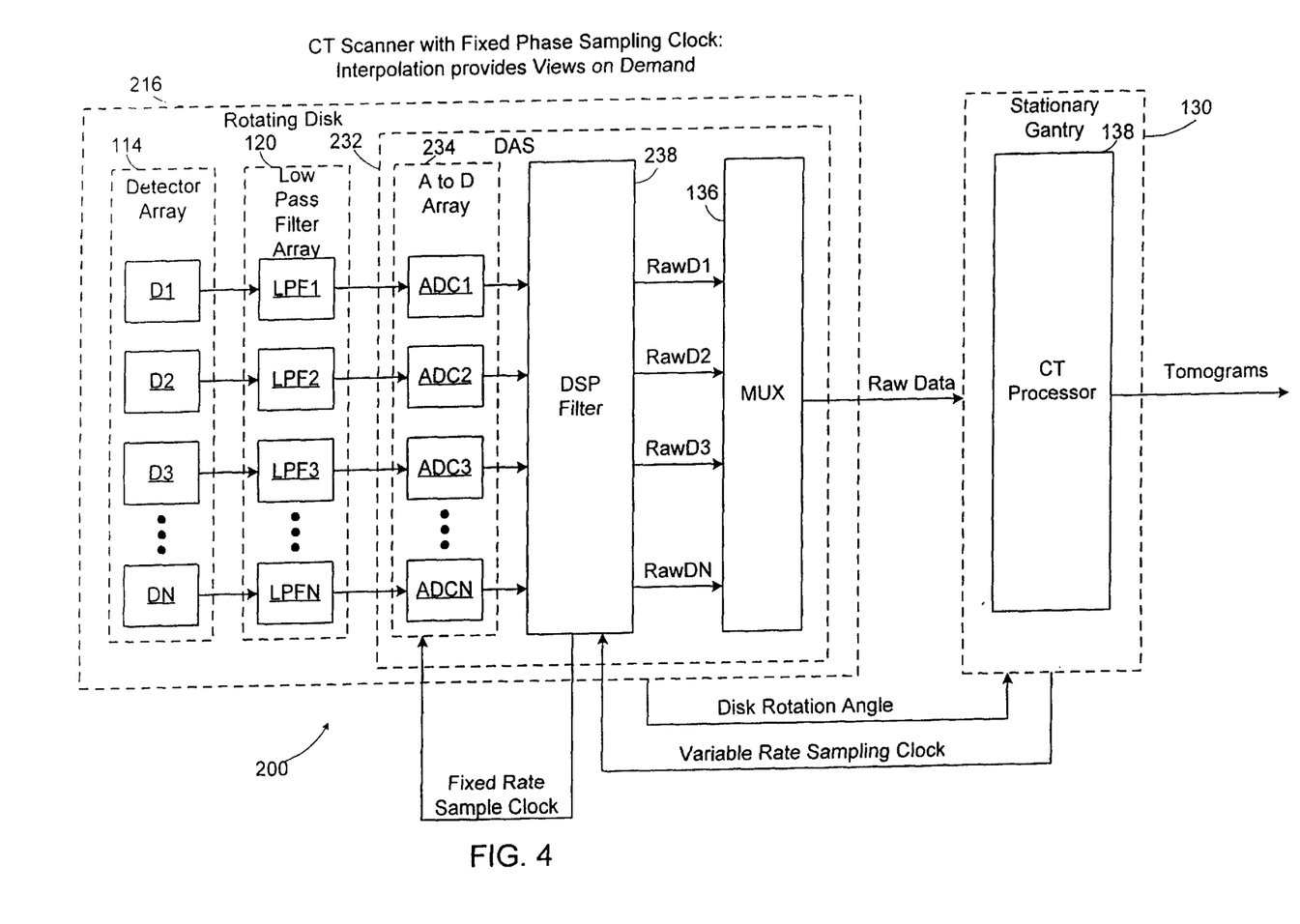
FIG. 4 shows a block diagram of a portion of a preferred embodiment of a part of a CT scanner constructed according to the invention.

FIG. 4 shows a block diagram of a CT scanner 200 constructed according to the invention. Scanner 200 is similar to prior art scanner 100 (shown in FIG. 3), however, scanner 200 includes rotating disk 216, modified in accordance with the present invention. Detector array 114, low pass filter array 120, an X-ray source (not shown), and an improved DAS 232 are mounted to and rotate with disk 216. Improved DAS 232 includes an array 234 of analog-todigital converters, a Digital Signal Processing (DSP) filter 238, and multiplexer 136.

The N analog output signals generated by detector array 114 are applied to low pass filter array 120, which in turn generates N filtered signals. The ith analog-to-digital converter ADCi in array 234 receives the filtered signal generated by the ith low pass filter LPFi and generates therefrom a digital output signal, for all i from one to N. The digital output signal generated by the ith converter ADCi in array 234 includes a set of digital samples, or data points, ADCi (Tj) generated at sampling times Tj. The data points generated by converter array 234 are applied to DSP filter 238 which generates therefrom the raw data signals (or projection data). DSP filter 238 also generates a constant frequency, stable phase Fixed Rate Sample Clock Signal that is applied to the analog-to-digital converter array 234. In scanner 200, the Variable Rate Sample Clock signal generated by processor 138 is applied to DSP filter 238 rather than to the analog-to-digital converter array 134 as was the case in the prior art scanner 100.

In scanner 200, the analog-to-digital converter array 234 samples the filtered signals generated by the low pass filter array 120 at a constant sampling rate or frequency under control of the Fixed Rate Sample Clock signal. Since the analog-to-digital digital converters in array 234 operate at a constant frequency, they may be simpler and less expensive than the converters in array 134 used in scanner 100 which necessarily operate at using a variable sampling rate or frequency. So unlike scanner 100, in scanner 200 the time $\Delta$ between generation of two adjacent data points ADCi(Tj) and ADCi(T{j+1}) is equal for all j. However, since the analog-to-digital converters in array 234 operate at a constant frequency, there is no guarantee that the sample times Tj will coincide with the times when projections should be generated. In particular, gantry 130 may request via the Variable Rate Sampling Clock signal that the DAS 232 generate a projection at a time Tj+$\delta$ (where $\delta$ can be positive or negative).

DSP filter 238 preferably generates the data points for such a projection at the corresponding time Tj+$\delta$ (where $\delta$ can be positive or negative) by interpolating a neighborhood of temporally proximal data points generated by converter array 234. More specifically, DSP filter 238 preferably generates a data point RawDi(Tj+$\delta$) in a projection according to the following Equation (1), where the projection includes all the data points RawDi(Tj+$\delta$) for all i from one to N.

$$RawDi(Tj + \delta) = \sum_{k=j-\frac{Size}{2}}^{j+\frac{Size}{2}} W(Tj + \delta, k) * ADCi(Tk) \qquad (1)$$

In the above Equation (1), the amount $\delta$ is assumed to be greater than or equal to $-\Delta/2$ and to be less than or equal to $+\Delta/2$ (i.e., the range for $\delta$ does not exceed the size of the interval between the generation of temporally adjacent data points ADCi(Tj) and ADCi(T{j+1})); the constant Size represents the size of the temporal neighborhood used by DSP filter 238 for interpolation of the data points RawDi (Tj+$\delta$); and the weights W(Tj+$\delta$,k) are selected by filter 238 according to a function of $\delta$.

In accordance with at least one aspect of the invention, scanner 200 effectively decouples data acquisition from projection data generation. Data acquisition is preformed at a constant rate or frequency by detector array 114, filter array 120, and converter array 234. So the same transfer function is used to generate each data point generated by converter array 234. Projection data generation is performed by DSP filter 238 under control of the Variable Rate Sampling Clock signal. Whenever processor 138 determines that it requires a projection (i.e., whenever the Disk Rotation Angle signal increases by $\Delta\theta$), DSP filter 238 generates the desired projection by interpolation of the acquired data.

Figure 5A:
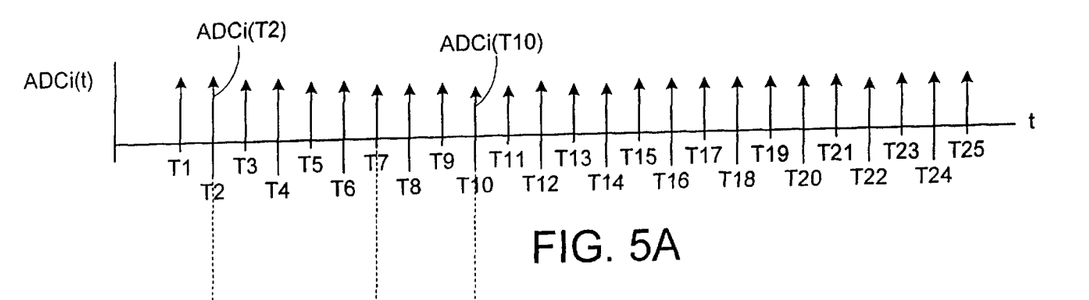
FIGS. 5A, 5B, 5C, and 5D show graphs that illustrate the operation of the DSP filter of the scanner shown in FIG. 4.
Figure 5B:
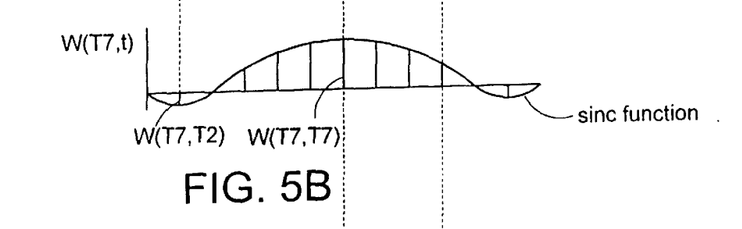
Figure 5C:
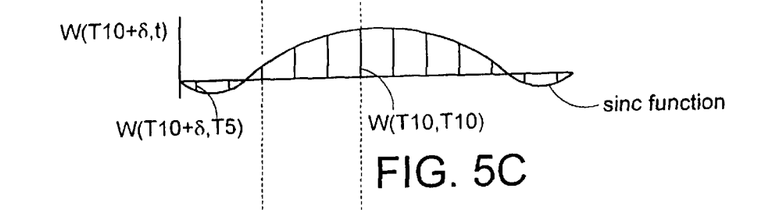

Those skilled in the art will appreciate that the weights W(Tj+$\delta$,k) in the above Equation (1) define the interpolation function used by DSP filter 238. In one preferred embodiment, the weights W(Tj+$\delta$,k) are selected so that DSP filter 238 performs its interpolation according to a sinc (i.e., sin(x)/x) function. FIGS. 5A, 5B, and 5C illustrate the operation of DSP filter 238. FIG. 5A shows a graph of an example of twenty five data points ADCi(Tj), for all j from one to twenty five. These data points are generated by an ith one of the analog-to-digital converters ADCi in array 234 for twenty-five successive projections. In FIG. 5A, the Y-axis represents amplitude and the X-axis represents time. The Fixed Rate Sample Clock signal causes the analog-to-digital converter ADCi to generate the data points ADCi(Tj) at regularly spaced sampling times Tj. The data points ADCi (Tj) are of course generated while the disk 216 is rotating around the patient during a CT scan. So each of the data points ADCi(Tj) has an associated sampling time and also an associated projection angle. As stated above, all the data points ADCi(Tj) are generated at regularly spaced sampling times. However, due to rotational irregularities in the disk rotation as illustrated in FIG. 2, the data points ADCi(Tj) are not necessarily generated precisely at regularly spaced projection angles.

Figure 5D:
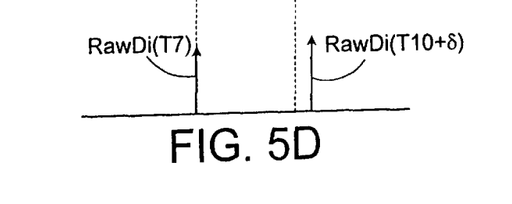

DSP filter 238 uses the data points ADCi(Tj) to generate the data points RawDi(Tj+$\delta$) at times Tj+$\delta$ that are determined by the Variable Rate Sampling Clock signal. FIGS. 5B and 5D illustrate the weights used by DSP filter 238 to generate a data point RawDi(T7), and FIGS. 5C and 5D illustrate the weights used by DSP filter 238 to generate a data point RawDi(T10+$\delta$). Since the weighting function shown in FIG. 5B is used to generate a data point RawDi (T7), this weighting function is centered about the sampling time T7. The domain of the weighting function extends from time T1 to time T13. The weights W(T7,T1), W(T7,T3), W(T7,T11), and W(T7,T13) are all equal to zero; the weights W(T7,T2) and W(T7,T12) are negative; and the weights W(T7,T4), W(T7,T5), W(T7,T6), W(T7,T7), W(T7, T8), W(T7,T9) and W(T7,T10) are all positive. DSP filter 238 generates the data point RawDi(T7) so that it is equal to the sum of W(T7,Tj)*ADCi(Tj) for all j from one to thirteen. Since the weighting function shown in FIG. 5C is used to generate the data point RawDi(T10+$\delta$), the weighting function is centered about the time T10+$\delta$. The domain of this weighting function extends from a time between sample times T4 and T5 to a time between sample times T16 and T17. So this weighting function is defined for sample times T5 through T16. In this weighting function, the weights W(T10+$\delta$,T5), W(T10+$\delta$,T6), W(T10+$\delta$,T15), and W(T10+ $\delta$T16) are negative; and the weights W(T10+$\delta$,T7), W(T10+ $\delta$,T8), W(T10+$\delta$,T9), W(T10+$\delta$,T10), W(T10+$\delta$,T11), W(T10+$\delta$,T12), W(T10+$\delta$,T13), and W(T10+$\delta$,T14) are positive. DSP filter 238 generates the data point RawDi (T10+$\delta$) so that it is equal to the sum of W(T10+$\delta$Tj)*ADCi (Tj) for all j from five to sixteen.

As those skilled in the art will appreciate, the DSP filter 238 may generate the weights for generation of a data point RawDi(t) at any arbitrary time t by centering the desired weighting function about the time t, and by then computing the values of the weighting function at the sample times Tj that fall within the domain of the weighting function. The weighting function illustrated in FIGS. 5B and 5C is a sinc type weighting function, and the domain (or temporal neighborhood size) of this function is equal to 13 times Δ. Those skilled in the art will appreciate that many different weighting functions and different temporal neighborhood sizes may be used in conjunction with the invention.

Figure 6:
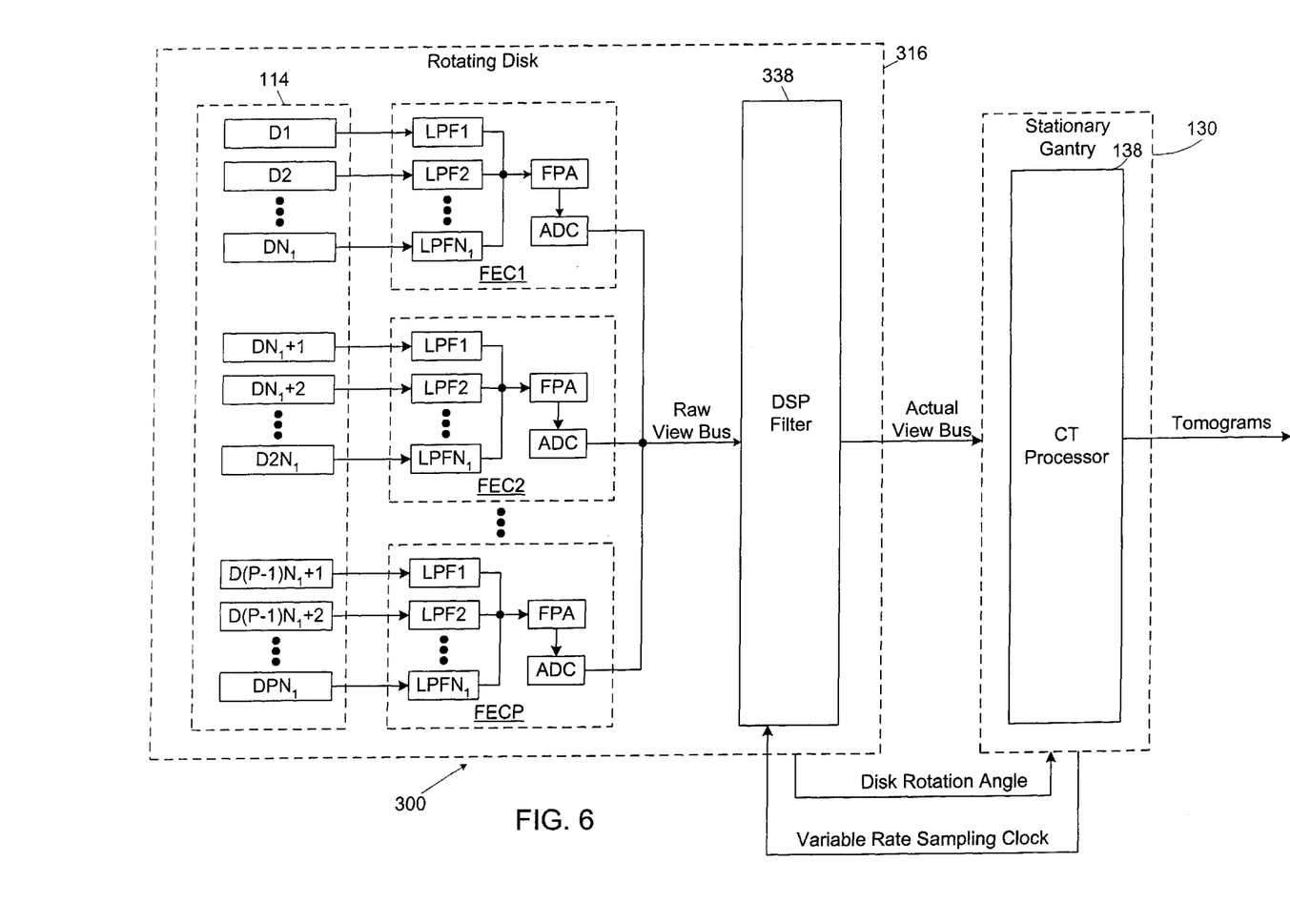
FIG. 6 shows a block diagram of a portion of a preferred embodiment of a CT scanner constructed according to the invention.

FIG. 6 shows a block diagram of a preferred embodiment of the relevant portion of a CT scanner 300 constructed according to the invention. Scanner 300 includes a rotating disk 316 and a stationary gantry 130. Detector array 114, an X-ray source (not shown), a set of P front end converter modules FECi for all i from one to P, and a DSP filter 338 are all mounted to and rotate with disk 316. The ith front end converter module FECi includes a set of $N_1$ low pass filters, a gain ranging or floating point amplifier FPA, and an analog-to-digital converter ADC, for all i from one to P. In one embodiment, $N_1$ is equal to sixty-four and P is equal to twenty-four, although other choices for these parameters are of course possible.

Each of the low pass filters in the front end converter modules receives the analog signal generated by a corresponding one of the detectors in array 114. In the ith front end converter module FECi, each of the low pass filters generates a filtered signal and all of the filtered signals are applied in a time multiplexed fashion to the floating point amplifier FPA, for all i from one to P. The floating point amplifier generates an output signal that is applied to the analog-to-digital converter. A floating point amplifier suitable for use with the invention is described for example in U.S. Pat. No. 5,053,770 issued Oct. 1, 1991 in the names of Eliot Mayer, Louis R. Poulo, Jeffrey L. Sauer and Hans J. Weedon, although other automatic floating point amplifiers can be used. The floating point amplifier is particularly useful where signals must be digitized to a high degree of resolution over a relatively large dynamic range of amplitudes, as is the case with CT scanners. Other floating point amplifiers may be utilized.

The analog-to-digital converters sample the signals generated by the floating point amplifiers and all of the samples are applied to DSP filter 338 via a Raw View Bus. The DSP filter 338 generates projections and applies them to the CT processor 138 of the stationary gantry 130 via an Actual View Bus.

In the ith front end converter module FECi, the analog-to-digital converter samples the output signal generated by each of the low pass filters at regular intervals of length $t_R$, for all i from one to P, where $t_R$ is given by the following Equation (2).

$$t_R = t_A * N_1 + t_z \quad (2)$$

In the above Equation (2), the variable $t_A$ represents the conversion time of the analog-to-digital converter (i.e., the time required for the analog-to-digital converter to generate a single sample), and the variable $t_z$ represents a fixed time interval between each set of $N_1$ samples generated by the analog-to-digital converter. During these fixed time intervals of length $t_z$, functions such as autozero or gain calibration may be performed to reset or calibrate the analog-to-digital converter.

So, in the ith front end converter FECi, the analog-to-digital converter generates a sequence of samples. Every interval of length $t_R$, the analog-to-digital converter generates one sample corresponding to each of the respective signals generated by the $N_1$ low pass filters during the sampling interval. Samples of the signals generated by any two of the low pass filters LPFi and LPF(i+k) of a module FECi are separated by a respective time interval of length $kt_A$.

Figure 7:
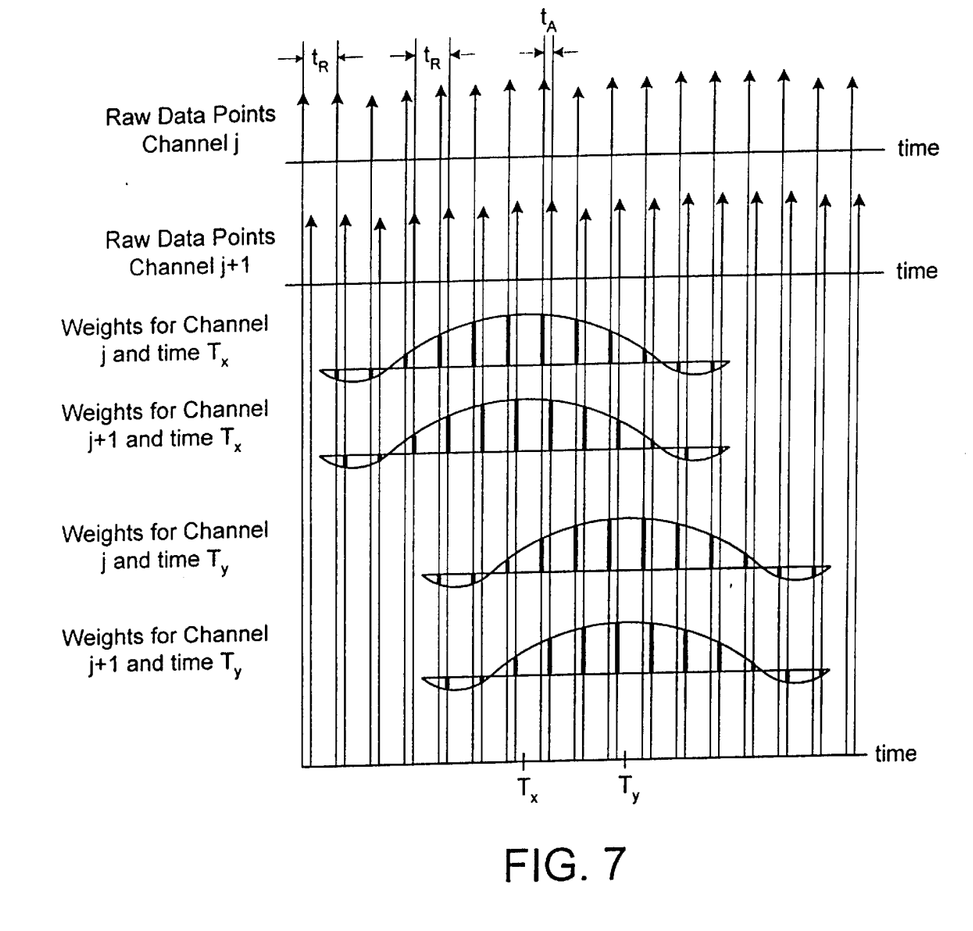
FIG. 7 shows a graph that illustrates the operation of the DSP filter shown in FIG. 6.

FIG. 7 shows a graph illustrating the operation of scanner 300. FIG. 7 shows an example of a set of data points indicated as the "Raw Data Points Channel j". Each of these data points is represented as a vertical arrow, and the height of the arrow represents the amplitude of the data points. Each of these data points is separated by a time interval of length $t_R$. These data points represent the samples generated by an analog-to-digital converter in one of the front end converter modules in response to the output signal generated by a jth one of the low pass filters in that converter module. FIG. 7 also shows a set of data points indicated as the "Raw Data Points Channel j+1". These data points represent the samples generated by an analog-to-digital converter in one of the front end converter modules in response to the (j+1)th one of the low pass filters in that converter module. Each of these data points is also separated by an interval of length $t_R$, and successive data points in the jth and (j+1)th channels are separated by an interval of length $t_A$. By time sequencing the outputs of the low pass filters of a converter module over the time interval $t_R$, the low pass filters of the module are able to share a common analog-to-digital converter with the converter converting on signal at a time. It is noted that alternatively a multiplexer can be connected between the outputs of the low pass filters of a module and the corresponding converter to achieve the same result.

FIG. 7 also shows the weights used by DSP filter 338 to generate data points at times $T_x$ and $T_y$ for each of the channels j and j+1. The weighting function used for generating data points at time $T_x$ is centered about time $T_x$, and the weighting function used for generating data points at time $T_y$ is centered about time $T_y$. As shown in FIG. 7, although the same weighting function is used for both channels j and j+1, the actual weights used for the two channels are slightly different because of the time offset of length $t_A$ between the data points in those channels.

Referring again to FIG. 6, whenever the processor 138 of gantry 130 requests a projection via the Variable Rate Sampling Clock signal, the DSP filter 338 uses a weighting function to interpolate a data point for all of the channels in scanner 300. DSP filter 338 applies these interpolated projections to processor 138 of the gantry 130 via the Actual View Bus. Scanner 300 is shown as not including a multiplexer (such as multiplexer 136 as shown in FIG. 4). As those skilled in the art will appreciate, the DSP filter 330 is capable of performing the time multiplexing operations that are performed by multiplexer 136 in scanner 200.

Figure 8:
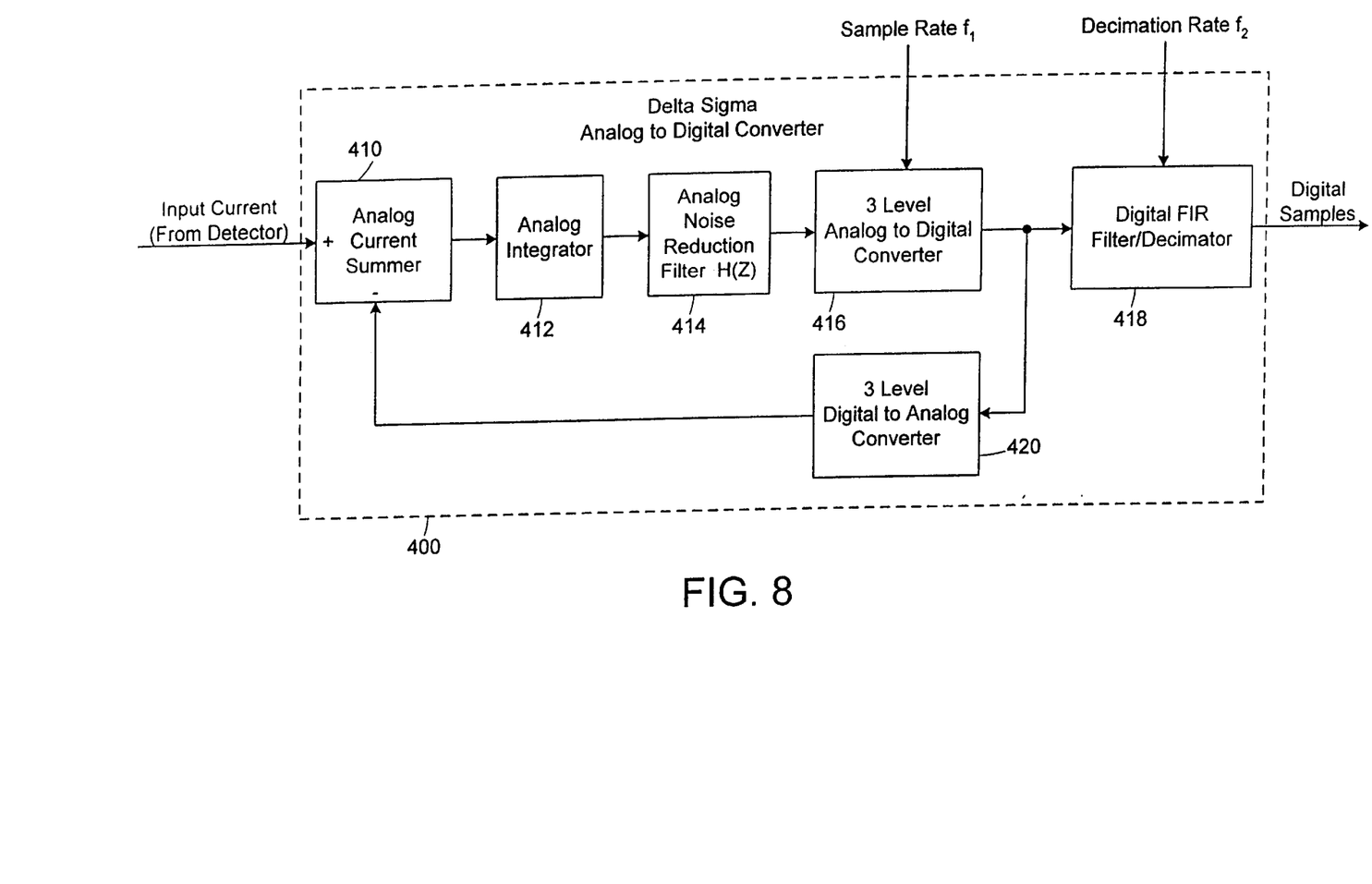
FIG. 8 shows a block diagram of a sigma-delta, analog-to-digital converter that may be used in conjunction with the invention.

In preferred CT scanners constructed according to the invention, the analog-to-digital converters used are delta-sigma type converters. FIG. 8 shows a block diagram of a delta-sigma analog-to-digital converter 400 that may be used in conjunction with the invention. Converter 400 includes an analog current summer 410, an analog integrator 412, an analog noise reduction filter 414, a three-level analog-to-digital converter 416, a digital finite impulse response (FIR) filter 418, and a three-level digital-to-analog converter 420. An analog current signal generated by a detector (or a low pass filter or a floating point amplifier depending on the particular implementation) is applied to a positive input terminal of current summer 410. An analog current signal generated by three-level digital-to-analog converter 420 is applied to a negative input terminal of current summer 410. The latter generates a difference signal by subtracting the value of the signal applied to its negative input terminal from the value of the signal applied to its positive input terminal, and applies this difference signal to the analog integrator 412. Integrator 412 generates an integrated signal representative of a time integral of the difference signal generated by summer 410. Analog noise reduction filter 414 filters the integrated signal to generate an output signal that is applied to three-level analog-to-digital converter 416. The latter generates a two bit digital signal that is applied to the input terminal of three-level digital-to-analog converter 420 and to the input terminal of FIR filter 418. FIR filter 418 generates the digital output signal of the converter 400 by essentially averaging or combining large numbers (e.g., three hundred eighty four) of the samples generated by the three-level converter 416.

Sigma-delta converters of the type shown in FIG. 8 as converter 400 are well known and are described, for example, in U.S. Pat. No. 5,274,375 issued Dec. 28, 1993, and co-pending application U.S. patent application Ser. No. 08/839,068, (which is a continuation of U.S. patent application Ser. No. 08/712,137, now abandoned, the latter application being a continuation of U.S. patent application Ser. No. 08/326,276, now abandoned) filed in the names of Bernard M. Gordon, Hans Weedon, Louis R. Poulo and Mark H. Miller, entitled a Data Acquisition System Using Delta-Sigma Analog-to-Digital Signal Converters, and assigned to the present assignee. In general, the three-level analog-to-digital converter 416 preferably generates samples at a frequency $f_1$ and the FIR filter 418 generates the samples of its output signal at a much lower frequency $f_2$. Other sigma-delta converters can be used, such as the one described in U.S. Pat. No. 5,142,286 issued to Ribner et al. on Aug. 25, 1992.

When sigma-delta converters are used in scanners constructed according to the invention, such as scanner 300 (shown in FIG. 6), the functionality of the DSP filter 338 may be incorporated into the FIR filters 418. However, even when the sigma-delta converters are used, it is ordinarily preferable to include the DSP filter 338 in scanners constructed according to the invention. This is because the FIR filter 418 used in a sigma-delta converter normally has hundreds of taps. Normally, the weights associated with the tap are constants. However, if the FIR filter 418 incorporates the functionality of DSP filter 338, the weights are not constants and instead are functions of δ. As those skilled in the art will appreciate, making these weights functions rather than constants significantly increases the cost and complexity of FIR filter 418. Since the DSP filter 338 normally uses many fewer weights than FIR filter 418, it is generally more economical to include the DSP filter 338 in which the weights are functions of the variable δ.

It should be appreciated that by inserting a DSP filter, such as shown at 238 and 338, for providing interpolation in the signal path, the data rate of the multi-channel DAS is effectively decoupled from determination of the projection angles required for accurate measurement. The data can be provided from the output of the DSP filter at arbitrary times consistent with accurately measured projection positions. The DSP filter also can provide correction of systematic errors in the position measurements. This last point is important because it allows much less expensive angle markings of the rotating disk. Thus, it is possible to measure the angles of the disk, store the deviations for incorrectly measured positions in the DSP memory and use the correction algorithm to not only correct the temporal position of the data, but also the corrected angular position of the data.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A CT scanner comprising:

analog-to-digital converter means for generating digital signals in response to analog signals representative of projection data taken at a relatively constant sampling rate; and means for generating projection data for a plurality of predetermined projection angles as a function of the digital signals irrespective of the constant sampling rate.

2. A scanner according to claim 1, wherein said analog-to-digital conversion means includes a plurality of analog-to-digital converters for generating a plurality of said digital signals in response to a plurality of said analog signals.

3. A scanner according to claim 1, wherein said analog-to-digital converter means includes a plurality of delta-sigma analog-to-digital converters.

4. A scanner according to claim 3, wherein each of said delta-sigma analog-to-digital converters includes means for receiving at least one of said analog current signals at its input.

5. A scanner according to claim 4, wherein each of said delta-sigma analog-to-digital converters includes a three level analog-to-digital converter.

6. A scanner according to claim 1, further including means for determining the timing of said predetermined projection angles relative to the timing of the generation of said digital signals by said analog-to-digital converter means.

7. A scanner according to claim 1, wherein said means for generating projection data for predetermined projection angles as a function of the digital signals includes means for interpolating the projection data for said predetermined projection angles as a weighted function of values of select ones of said digital signals.

8. A scanner according to claim 7, further including a plurality of detectors for generating a plurality of analog signals representative of x-ray absorption along predetermined ray paths for each of a plurality of projections during a scan, means for rotating said detectors through said plurality of predetermined projection angles, and means for determining the timing of the position of said detectors at said predetermined projection angles relative to the timing of the generation of said digital signals by said analog-to-digital converter means.

9. A scanner according to claim 8, wherein said analog-to-digital converter means generates a timed sequence of digital signals in response to successive ones of said analog signals for each of said detectors at said relatively constant sampling rate, and said means for interpolating the projection data for said predetermined projection angles includes means for interpolating said projection data for each of said detectors for each of said predetermined projection angles as a weighted function of values of a select number of the digital signals temporally spaced from the time when each such detector is positioned at the predetermined projection angle.

10. A scanner according to claim 8, wherein said means for interpolating the projection data for said predetermined projection angles includes means for interpolating said projection data for each of said detectors for each of said predetermined projection angles in accordance with the following function:

$$RawDi(Tj+\delta) = \sum_{k=j-\frac{Size}{2}}^{j+\frac{Size}{2}} W(Tj+\delta,k) * ADCi(Tk) \qquad (1)$$

wherein ADCi(Tj) represent the various data points provided by the values of said digital signals;

Δ is the amount of time difference between successive digital signals;

δ is difference between the angle of a detector when a sample is generated and the angle of the detector when the detector as a predetermined projection angle;

the constant Size represents the size of the temporal neighborhood used for interpolation of the data points RawDi(Tj+δ); and the weights W(Tj+δ,k) are selected according to a function of δ, the range for δ not exceeding the size of the time interval between generation of temporally adjacent data points ADCi(Tj) and ADCi(T{j+1})).

11. A data acquisition system for use in a CT scanner, said system comprising:

analog-to-digital converter means for generating digital signals in response to analog signals representative of projection data taken at a relatively constant sampling rate; and means for generating projection data for a plurality of predetermined projection angles as a function of the digital signals irrespective of the constant sampling rate.

12. A system according to claim 11, wherein said analog-to-digital conversion means includes a plurality of analog-to-digital converters for generating a plurality of said digital signals in response to a plurality of said analog signals.

13. A system according to claim 11, wherein said analog-to-digital converter means includes a plurality of delta-sigma analog-to-digital converters.

14. A system according to claim 13, wherein each of said delta-sigma analog-to-digital converters includes means for receiving at least one of said analog current signals at its input.

15. A system according to claim 14, wherein each of said delta-sigma analog-to-digital converters includes a three level analog-to-digital converter.

16. A system according to claim 11, further including means for determining the timing of said predetermined projection angles relative to the timing of the generation of said digital signals by said analog-to-digital converter means.

17. A system according to claim 11, wherein said means for generating projection data for predetermined projection angles as a function of the digital signals includes means for interpolating the projection data for said predetermined projection angles as a weighted function of values of select ones of said digital signals.

18. A system according to claim 17, further including a plurality of detectors for generating a plurality of analog signals representative of x-ray absorption along predetermined ray paths for each of a plurality of projections during a scan, means for rotating said detectors through said plurality of predetermined projection angles, and means for determining the timing of the position of said detectors at said predetermined projection angles relative to the timing of the generation of said digital signals by said analog-to-digital converter means.

19. A system according to claim 18, wherein said analog-to-digital converter means generates a timed sequence of digital signals in response to successive ones of said analog signals for each of said detectors at said relatively constant sampling rate, and said means for interpolating the projection data for said predetermined projection angles includes means for interpolating said projection data for each of said detectors for each of said predetermined projection angles as a weighted function of values of a select number of the digital signals temporally spaced from the time when each such detector is positioned at the predetermined projection angle.

20. A system according to claim 18, wherein said means for interpolating the projection data for said predetermined projection angles includes means for interpolating said projection data for each of said detectors for each of said predetermined projection angles in accordance with the following function:

$$RawDi(Tj+\delta) = \sum_{k=j-\frac{Size}{2}}^{j+\frac{Size}{2}} W(Tj+\delta,k) * ADCi(Tk) \qquad (1)$$

wherein ADCi(Tj) represent the various data points provided by the values of said digital signals;

Δ is the amount of time difference between successive digital signals;

δ is difference between the angle of a detector when a sample is generated and the angle of the detector when the detector as a predetermined projection angle;

the constant Size represents the size of the temporal neighborhood used for interpolation of the data points RawDi(Tj+δ); and the weights W(Tj+δ,k) are selected according to a function of δ, the range for δ not exceeding the size of the time interval between generation of temporally adjacent data points ADCi(Tj) and ADCi(T{j+1})).

* * * * *